United States Patent
Mordehai et al.

(10) Patent No.: US 9,482,642 B2
(45) Date of Patent: Nov. 1, 2016

(54) FAST METHOD FOR MEASURING COLLISION CROSS SECTION OF IONS UTILIZING ION MOBILITY SPECTROMETRY

(71) Applicant: Agilent Technologies, Inc., Santa Clara, CA (US)

(72) Inventors: Alexander Mordehai, Santa Clara, CA (US); Ruwan T. Kurulugama, Santa Clara, CA (US); Christian Klein, Santa Clara, CA (US); John Fjeldsted, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 238 days.

(21) Appl. No.: 14/170,068

(22) Filed: Jan. 31, 2014

(65) Prior Publication Data

US 2015/0219598 A1    Aug. 6, 2015

(51) Int. Cl.
    *H01J 49/00*       (2006.01)
    *G01N 27/62*     (2006.01)

(52) U.S. Cl.
    CPC ......... *G01N 27/622* (2013.01); *H01J 49/0031* (2013.01); *H01J 49/0009* (2013.01)

(58) Field of Classification Search
None
See application file for complete search history.

(56) References Cited

U.S. PATENT DOCUMENTS

| | | | | |
|---|---|---|---|---|
| 5,426,056 A * | 6/1995 | Nacson | ........... | G01N 27/626 250/281 |
| 6,124,592 A * | 9/2000 | Spangler | ........... | G01N 27/624 250/282 |
| 8,173,959 B1 * | 5/2012 | Boumsellek | ........... | G01N 27/622 250/281 |
| 9,082,596 B2 * | 7/2015 | Brown | ........... | G01N 27/622 |
| 2008/0173809 A1 * | 7/2008 | Wu | ........... | C07B 63/00 250/283 |
| 2009/0236514 A1 * | 9/2009 | Renner | ........... | G01N 27/64 250/282 |
| 2010/0127163 A1 * | 5/2010 | Zhdaneev | ........... | G01N 1/38 250/282 |
| 2011/0127417 A1 * | 6/2011 | Ibrahim | ........... | H01J 49/004 250/282 |
| 2012/0273669 A1 * | 11/2012 | Ivashin | ........... | G01N 27/626 250/282 |
| 2012/0326020 A1 * | 12/2012 | Ivashin | ........... | G01N 27/622 250/282 |
| 2013/0264475 A1 * | 10/2013 | Ivashin | ........... | H01J 49/105 250/290 |
| 2013/0306855 A1 * | 11/2013 | Raptakis | ........... | H01J 49/025 250/282 |
| 2014/0034844 A1 * | 2/2014 | Ivashin | ........... | H01J 31/04 250/397 |
| 2015/0090873 A1 * | 4/2015 | Brown | ........... | G01N 27/622 250/282 |
| 2015/0219598 A1 * | 8/2015 | Mordehai | ........... | G01N 27/622 250/282 |

OTHER PUBLICATIONS

Siu, C-K.; Optimization of Parameters Used in Algorithms of Ion-Mobility Calculation for Conformational Analyses; J. Phys. Chem. B, 2010, 114, 1204-1212; 9 pages.

(Continued)

*Primary Examiner* — Andrew Smyth (57) ABSTRACT

The collision cross section (CCS) of a sample ion may be calculated by measuring a total drift time taken by the sample ion to travel through an ion mobility spectrometry drift cell to an ion detector. The CCS may be calculated based on the total drift time measured, and on a proportionality coefficient that defines the time taken by the sample ion to travel through a mobility dominated region between the drift cell and the detector. The proportionality coefficient may be determined from measuring the total drift times of reference ions. Calculation of the CCS of the sample ion may also be based on a proportionality coefficient that defines the time taken by the sample ion to travel through a mobility-independent region where the velocity of the ion depends on the electrostatic field strength, mass and the charge state of the ion.

20 Claims, 4 Drawing Sheets

(56) References Cited

OTHER PUBLICATIONS

Wu, C. et al.; Atmospheric Pressure Ion Mobility Spectrometry of Protonated and Sodiated Peptides; Rapid Commun. Mass Spectrom. 13, 1138-1142, 1999. 5 pages.

Kurulugama, R. et al.; The Agilent Ion Mobility Q-TOF Mass Spectrometer System; Technical Overview, 2013; Agilent Technologies, Inc., 5991-3244EN; 12 pages.

Creaser, C.S. et al.; Gas-phase ion mobility studies of amines and polyether/amine complexes using tandem quadrupole ion trap/ion mobility spectrometry; Eur. J. Mass Spectrom. 6, 213-218; 2000; 6 pages.

Clemmer, D. E. et al.; Ion Mobility Measurements and their Applications to Clusters and Biomolecules; J. Mass Spectrometry, vol. 32, 577-592 (1997); John Wiley & Sons, Ltd.; 16 pages.

Hoaglund-Hyzer, C. S. et al.; Anhydrous Protein Ions, Chem. Rev. 1999, 99, 3037-3079 (1999); 44 pages.

\* cited by examiner

FAST METHOD FOR MEASURING COLLISION CROSS SECTION OF IONS UTILIZING ION MOBILITY SPECTROMETRY

TECHNICAL FIELD

The present invention relates generally to ion mobility spectrometry (IMS) and ion mobility-mass spectrometry (IM-MS). The invention relates particularly to method development for measuring (calculating) the collision cross section (CCS) of analyte ions utilizing IM-MS instrumentation.

BACKGROUND

Ion mobility spectrometry (IMS) is a gas-phase ion separation technique in which ions become separated in time as they travel through a drift cell (drift tube) of known length containing a buffer gas (drift gas) of known composition (e.g., nitrogen), pressure and temperature. During this travel, the ions become separated based on their different collision cross sections (CCSs), which can be correlated to their differing mobilities through the buffer gas. An IMS system in general includes an ion source for ionizing molecules of a sample of interest, followed by the drift cell that receives the ions, followed by an ion detector for counting the separated ions. The ion detector communicates with electronics configured for processing output signals from the ion detector as needed to produce a user-interpretable drift spectrum. The drift spectrum is typically presented as a plot containing a series of peaks indicative of the relative abundances of detected ions as a function of their drift time through the drift cell. The drift spectrum may be utilized to identify and distinguish different analyte species of the sample.

IMS may be coupled with one or more other types of separation techniques to increase compound identification power, such as gas chromatography (GC), liquid chromatography (LC), or mass spectrometry (MS). For example, an IMS drift cell may be coupled in-line with an MS system to form a combined IM-MS system. An MS system in general includes a mass analyzer for separating ions based on their differing mass-to-charge ratios (or m/z ratios, or more simply "masses"), followed by an ion detector. An MS analysis produces a mass spectrum, which is a series of peaks indicative of the relative abundances of detected ions as a function of their m/z ratios. The mass spectrum may be utilized to determine the molecular structures of components of the sample. An IMS drift cell is often coupled to a time-of-flight mass spectrometer (TOF MS), which utilizes a high-resolution mass analyzer (TOF analyzer) in the form of an electric field-free flight tube. An ion extractor (or pulser) injects ions in pulses (or packets) into the flight tube. Ions of differing masses travel at different velocities through the flight tube and thus separate (spread out) according to their differing masses, enabling mass resolution based on time-of-flight.

In the combined IM-MS system, the ion source is followed by the IMS drift cell, which is followed by the mass analyzer and then the ion detector. Thus, ions are separated by mobility prior to being transmitted into the MS where they are then mass-resolved. Performing the two separation techniques in tandem is particularly useful in the analysis of complex chemical mixtures, including biopolymers such as polynucleotides, proteins, carbohydrates and the like, as the added dimension provided by the IM separation may help to separate ions that are different from each other but present overlapping mass peaks. This hybrid separation technique may be further enhanced by coupling it with LC, thus providing an LC-IM-MS system.

In low-field drift-time IMS techniques, ions travel through the drift cell under the influence of a uniform DC voltage gradient established by electrodes of the drift cell. Typical electric fields utilized for low-field IMS techniques include, but are not limited to, 10 to 20 V/cm, and typical buffer gas pressures include, but are not limited to, 1 to 760 Torr. While the electric field moves the ions through the drift cell, the ions experience a drag force due to collisions with the stationary buffer gas molecules in the drift cell. The drag force acts against the electrical force that moves the ions. The drag force experienced by an ion depends on its collision cross section (CCS or $\Omega$), which is a function of the size and shape of the ion, and on its electrical charge and mass. Multiply charged ions move through the buffer gas more effectively than singly charged ions because multiply charged ions experience a greater force due to the electrical field. Ions with larger CCSs are retarded more easily by collisions with the buffer gas. After entering the drift cell, an equilibrium state between the drag force and electrical force is quickly reached and the ions start moving with constant drift velocity $V_d$, which is proportional to the applied electric field of strength E as follows:

$$V_d = KE, \quad (1)$$

where the proportionality constant K is the gas phase mobility of an ion, typically given in units of $cm^2 \times V^{-1} \times s^{-1}$. To account for differences in the pressure and temperature of the buffer gas, the mobility K may be expressed as reduced mobility $K_o$ in which the pressure P (in Torr) and temperature T (in Kelvin) of the buffer gas are normalized, as follows:

$$K_O = \frac{L}{t_d E} \frac{P}{760} \frac{273.2}{T}, \quad (2)$$

where the ion drift velocity is expressed in terms of the length L of the drift cell and the drift time $t_d$ (in ms) of the ion through the drift cell, 760 Torr is standard pressure, and 273.2 Kelvin is standard temperature. Thus, the mobility of an ion of interest may be calculated experimentally by measuring the ion's drift time $t_d$, i.e., the time taken by the ion to traverse the drift cell of known length L and applied electric field strength E.

If the drift time of an ion through the drift cell, the pressure in the drift cell, and the voltage across the drift cell are known, then one can calculate the CCS of the ion. This CCS parameter is specific for the ion and is instrument-independent, and therefore can be utilized as a unique parameter for compound identification. The CCS parameter is of great interest in structural characterization of molecules, theoretical molecular dynamic simulations, and other fields of inquiry. Reduced mobility $K_o$ can be related to CCS, $\Omega$ (typically in Angstroms squared, $Å^2$), through the Mason-Schamp equation:

$$K_O = \frac{(18\pi)^{1/2}}{16} \frac{ze}{(k_b T)^{1/2}} \left[ \frac{1}{m_I} + \frac{1}{m_B} \right]^{1/2} \frac{1}{N} \frac{1}{\Omega}, \quad (3)$$

where ze is the charge on the ion, $k_b$ is the Boltzmann constant, T is the temperature, $m_I$ the mass of the ion, $m_B$ is the mass of the buffer gas molecule, and N is the number density of the buffer gas. It is seen that ion mobility is directly proportional to the charge on the ion and inversely proportional to the CCS of the ion. The CCS may be calculated directly from experimentally determined variables such as drift time $t_d$ by combining equations (2) and (3) and solving for $\Omega$, as follows:

$$\Omega = \frac{(18\pi)^{1/2}}{16} \frac{ze}{(k_bT)^{1/2}} \left[\frac{1}{m_I} + \frac{1}{m_B}\right]^{1/2} \frac{t_dE}{L} \frac{760}{P} \frac{T}{273.2} \frac{1}{N}. \quad (4)$$

In a typical ion mobility based system, there is some distance over which an ion travels from the exit of the drift cell to the ion detector, and over which the ion's flight is not appreciably influenced by mobility. For example, in a hybrid IM-MS system it takes additional time for an ion to reach the detector due to ion optical elements existing between the drift cell and the mass analyzer/detector. Thus, the observed drift time of an ion as measured by the detector, $t_D$, is greater than the actual time the ion took to travel through the drift cell, $t_d$. Thus, the drift time $t_d$ utilized in the Mason-Schamp equation to calculate the CCS of the ion is a "corrected" drift time, which may be found from the following relation:

$$t_d = t_D - t_0, \quad (5)$$

where $t_0$ is the time the ion spent traveling from the exit of the drift cell to the ion detector. The proper calculation of time $t_0$ is crucial for the accuracy of CCS measurements.

Conventionally, time $t_0$ is calculated by performing several ion mobility experiments at different drift field strengths, E (V/cm) and plotting observed (measured) drift time $t_D$ (y-axis) over the inverse of the applied drift voltage (1/V) (or over field strength (1/E)) (x-axis). The resulting plot is a set of data points (1/V, $t_D$) lying along a straight line showing the linear correlation between observed drift time and inverse applied drift field/voltage. The intercept of this plot with the y-axis (drift time axis) is the time $t_0$ for the ion of interest.

The common practice is to employ at least five different drift voltages and perform at least five ion mobility experiments (frames) at each drift voltage for one CCS experiment. Assuming it takes about 60 ms to perform one ion mobility experiment, the total measurement time required would be about 1.5 s. Unfortunately, such an amount of measurement time is unacceptably long for many situations. For example, such an amount of measurement time is not very compatible with modern chromatography, as the chromatographic peak width may be as short as 1 s, with peak widths of 3 s being quite common.

Therefore, there is a need for providing a method for faster CCS measurement, particularly one that is compatible with the time scale of chromatographic separation.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for measuring the collision cross section (CCS) of a sample ion includes: measuring a total drift time taken by the sample ion to travel through an ion mobility spectrometry drift cell to an ion detector; and calculating the CCS of the sample ion based on the total drift time measured and on a proportionality coefficient that relates to an external drift time taken by the sample ion to travel through a mobility dominated region outside the drift cell.

According to another embodiment, a method for acquiring spectral data from a sample includes: producing a plurality of sample ions from the sample; transmitting the sample ions through the drift cell to separate sample ions of differing CCSs; transmitting the sample ions from the drift cell through a mass analyzer to separate sample ions of differing m/z ratios; transmitting the sample ions from the mass analyzer to the ion detector; calculating CCSs of the respective sample ions according to any of the methods disclosed herein; and generating a drift time spectrum and a mass spectrum from signals outputted by the ion detector.

According to another embodiment, an ion mobility-mass spectrometry (IM-MS) system is configured for performing all or part of any of the methods disclosed herein.

According to another embodiment, an ion mobility-mass spectrometry (IM-MS) system includes: an IM drift cell comprising a drift cell entrance and a drift cell exit; an intermediate region following the drift cell exit and comprising a mobility-dependent region; an MS detector following the intermediate region; and a computing device configured for measuring the collision cross section (CCS) of a sample ion by: measuring a total drift time taken by the sample ion to travel from the drift cell entrance to the ion detector; and calculating the CCS of the sample ion based on the total drift time measured and on a proportionality coefficient relating to a drift time taken by the sample ion to travel through the drift cell and through the mobility-dependent region.

According to another embodiment, a system for measuring the collision cross section (CCS) of a sample ion includes at least a processor and a memory configured for performing all or part of any of the methods disclosed herein.

According to another embodiment, a computer-readable storage medium includes instructions for performing all or part of any of the methods disclosed herein.

According to another embodiment, a system includes the computer-readable storage medium.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1A:
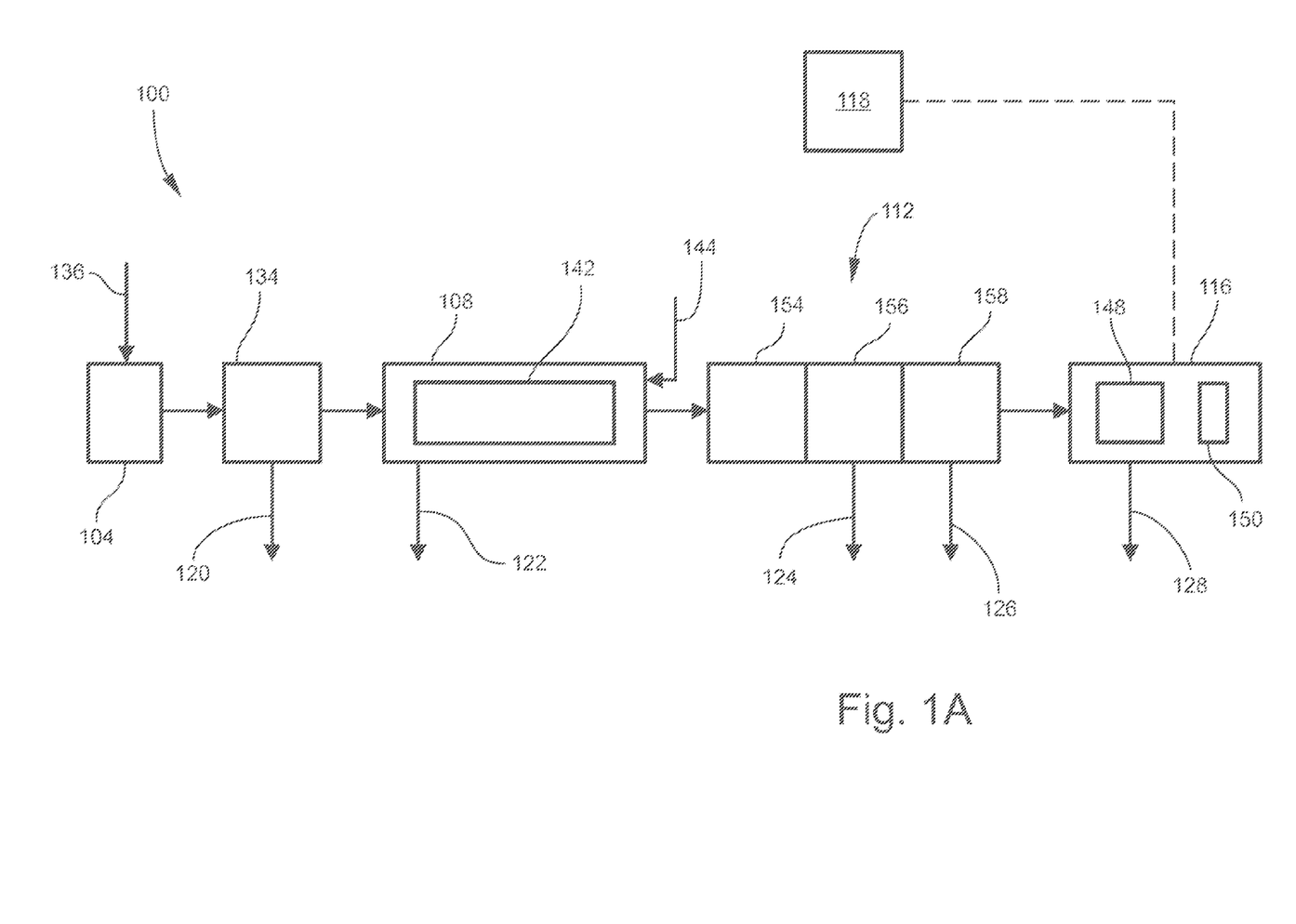
FIG. 1A is a schematic view of an example of an ion mobility-mass spectrometry (IM-MS) system according to some embodiments, and which may be utilized in the implementation of the subject matter described herein.

FIG. 1A is a schematic view of an example of an ion mobility-mass spectrometry (IM-MS) system 100 according to some embodiments, and which may be utilized in the implementation of the subject matter described herein. The IM-MS system 100 may be considered as a non-limiting example of an operating environment in which to perform methods for calculating the collision cross section (CCS) of one or more ions of interest. Representative embodiments of such methods are described by way of example below.

The IM-MS system 100 generally includes an ion source 104, an IMS 108, and an MS 116. The IM-MS system 100 may also generally include an ion processing 112 between the IMS 108 and the MS 116, which is described further below. The IM-MS system 100 may also include an ion trap and/or ion gate 134 between the ion source 104 and the IMS 108. In some embodiments in which the ion source 104 is configured for outputting pulses or packets of ions, the ion trap and/or ion gate 134 may not be included. The IM-MS system 100 also includes a vacuum system for maintaining various interior regions of the IM-MS system 100 at controlled, sub-atmospheric pressure levels. The vacuum system is schematically depicted by vacuum lines 120-128. The vacuum lines 120-128 are schematically representative of one or more vacuum-generating pumps and associated plumbing and other components appreciated by persons skilled in the art. The vacuum lines 120-128 may also remove any residual non-analytical neutral molecules from the ion path through the IM-MS system 100. The IM-MS system 100 may also include a computing device 118 configured for controlling various components of the IM-MS system 100, and which may be further configured for providing and controlling a user interface. The operation and design of various components of IM-MS systems are generally known to persons skilled in the art and thus need not be described in detail herein. Instead, certain components are briefly described to facilitate an understanding of the subject matter presently disclosed.

The ion source 104 may be any type of continuous-beam or pulsed ion source suitable for producing analyte ions for spectrometry. Examples of ion sources 104 include, but are not limited to, electrospray ionization (ESI) sources, other atmospheric pressure ionization (API) sources, photo-ionization (PI) sources, electron ionization (EI) sources, chemical ionization (CI) sources, field ionization (FI) sources, plasma or corona discharge sources, laser desorption ionization (LDI) sources, and matrix-assisted laser desorption ionization (MALDI) sources. In some embodiments, the ion source 104 may include two or more ionization devices, which may be of the same type or different type. Depending on the type of ionization implemented, the ion source 104 may reside in a vacuum chamber or may operate at or near atmospheric pressure. Sample material to be analyzed may be introduced to the ion source 104 by any suitable means, including hyphenated techniques in which the sample material is an output 136 of an analytical separation instrument such as, for example, a gas chromatography (GC) or liquid chromatography (LC) instrument (not shown). Generally, the inclusion of a GC or LC instrument determines which types of ionization techniques are appropriate for the IM-MS system 100.

The IMS 108 includes a drift cell 142 enclosed in a chamber. The chamber communicates with a pump that maintains the drift cell 142 at a buffer (drift) gas pressure ranging from, for example, 1 to 760 Torr. A gas inlet 144 directs an inert buffer gas (e.g., nitrogen) into the drift cell chamber. The drift cell 142 includes a series of drift cell electrodes (typically ring-shaped) spaced along the axis. The drift cell electrodes are in signal communication with a voltage source to generate a DC voltage gradient along the axis. As noted above, the axial DC voltage gradient moves the ions through the drift cell 142 in the presence of the drift gas, whereby the ions become separated in time based on their different CCSs. The DC voltage gradient may be generated in a known manner, such as by applying a voltage between the first and last drift cell electrodes, and through a resistive divider network between the first and last drift cell electrodes, such that successively lower voltages are applied to the respective drift cell electrodes along the length of the drift cell 142.

The MS 116 may generally include a mass analyzer 148 and an ion detector 150 enclosed in a chamber. The vacuum line 128 maintains the interior of the mass analyzer 148 at very low (vacuum) pressure. In some embodiments, the mass analyzer 148 pressure ranges from $10^{-4}$ to $10^{-9}$ Torr. The mass analyzer 148 may be any device configured for separating, sorting or filtering analyte ions on the basis of their respective m/z ratios. Examples of mass analyzers include, but are not limited to, multipole electrode structures (e.g., quadrupole mass filters, ion traps, etc.), time-of-flight (TOF) analyzers, ion cyclotron resonance (ICR) traps, and electric field or magnetic field based sector instruments. The ion detector 150 may be any device configured for collecting and measuring the flux (or current) of mass-discriminated ions outputted from the mass analyzer 148. Examples of ion detectors 150 include, but are not limited to, multi-channel plates, electron multipliers, photomultipliers, and Faraday cups.

Generally, the ion processing section 112 may be considered as a section between the exit of the drift cell 142 and the entrance of the mass analyzer 148 (e.g., the pulser of a TOF analyzer). Generally, the ion processing section 112 may be considered as being configured for receiving the ions eluting from the drift cell 142 and transferring the ions to the MS 116. As described below, the present disclosure accounts for the time an ion takes to traverse the ion processing section 112, i.e., the time spent by an ion between the drift cell 142 and the MS 116. The ion processing section 112 may include one or more components (structures, devices, regions, etc.) positioned between the drift cell 142 and the MS 116. These components may serve various functions such as, for example, pressure reduction, neutral gas removal, ion beam focusing/guiding, ion filtering/selection, ion fragmentation, etc. The exact combination of components making up the ion processing section 112 will vary from one IM-MS system design to another. In the illustrated example, the ion processing section 112 includes an ion funnel 154 that receives and focuses ions eluting from the drift cell 142, a quadrupole mass filter 156, and a collision cell 158. The ion processing section 112 may also include electrostatic ion optics (e.g., lenses) at one or more points along the ion path between the drift cell 142 and the MS 116. The ion processing section 112 may also be referred to herein as an "intermediate region" between the drift cell 142 and the ion detector (i.e., the MS 116).

Thus, in some embodiments the MS 116 in combination with the ion processing section 112 (or a portion thereof) may form a tandem MS or MS$^n$ system. As an example, a tandem MS may include a mass filter followed by a collision cell, which in turn is followed by a mass filter (e.g., a final mass filter or scanner in a triple-quad or QQQ system, or a TOF analyzer in a qTOF system).

The computing device 118 is schematically depicted as representing one or more modules or components configured for controlling, monitoring and/or timing various functional aspects of the IM-MS system 100 such as, for example, the ion source 104, the IMS 108, and the MS 116, as well as any vacuum pumps, ion optics, upstream LC or GC instrument, sample introduction device, etc., that may be provided in the IM-MS system 100 but not specifically shown in FIG. 1A. One or more modules or components may be, or be embodied in, for example, a desktop computer, laptop computer, portable computer, tablet computer, handheld computer, mobile computing device, personal digital assistant (PDA), smartphone, etc. The computing device 118 may also schematically represent all voltage sources not specifically shown, as well as timing controllers, clocks, frequency/waveform generators and the like as needed for applying voltages to various components of the IM-MS system 100. The computing device 118 may also be configured for receiving the ion detection signals from the ion detector 128 and performing tasks relating to data acquisition and signal analysis as necessary to generate chromatograms, drift spectra, and mass spectra characterizing the sample under analysis. The computing device 118 may also be configured for providing and controlling a user interface that provides screen displays of spectrometric data and other data with which a user may interact, as described below. The computing device 118 may include one or more reading devices on or in which a tangible computer-readable (machine-readable) medium may be loaded that includes instructions for performing all or part of any of the methods disclosed herein. For all such purposes, the computing device 118 may be in signal communication with various components of the IM-MS system 100 via wired or wireless communication links (as partially represented, for example, by a dashed line between the computing device 118 and the MS 116). Also for these purposes, the computing device 118 may include one or more types of hardware, firmware and/or software, as well as one or more memories and databases.

Figure 1B:
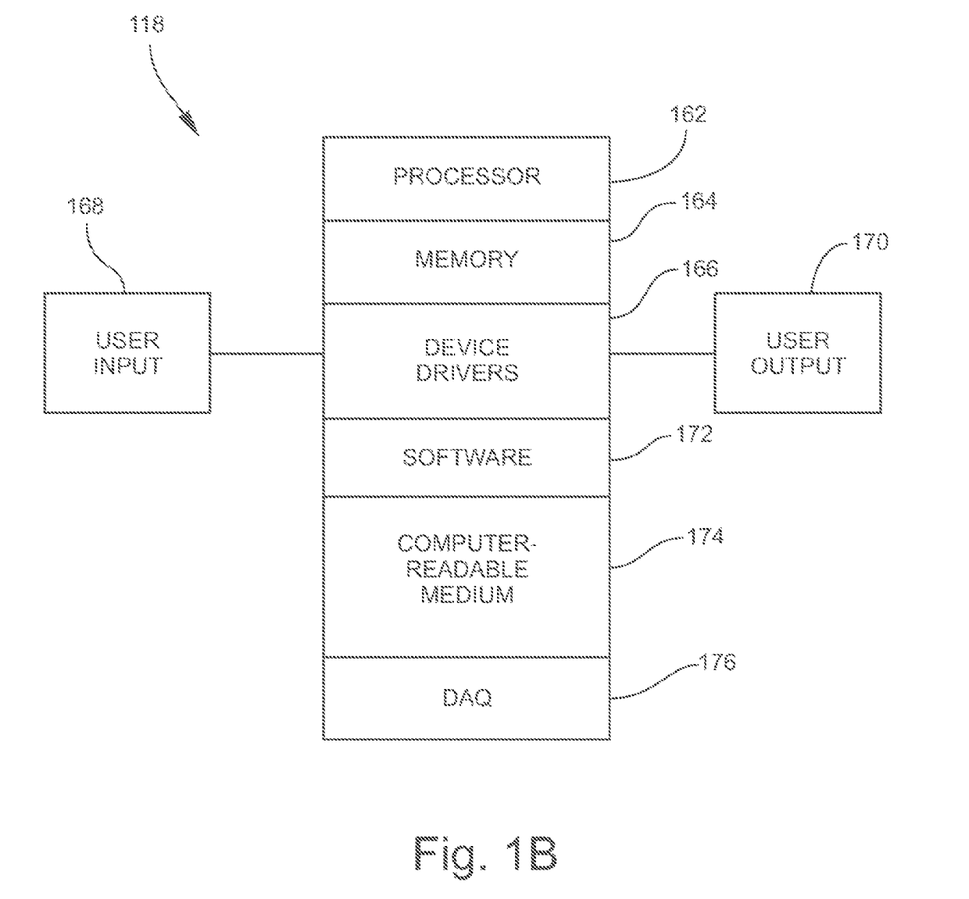
FIG. 1B is a schematic view of an example of a computing device that may be part of or communicate with the IM-MS system illustrated in FIG. 1A.

FIG. 1B is a schematic view of a non-limiting example of a computing device 118 that may be part of or communicate with an IM-MS system such as that illustrated in FIG. 1A. In the illustrated embodiment the computing device 118 includes a processor 162 (typically electronics-based), which may be representative of a main electronic processor providing overall control, and one or more electronic processors configured for dedicated control operations or specific signal processing tasks (e.g., a graphics processing unit, or GPU). The computing device 118 also includes one or more memories 164 (volatile and/or non-volatile) for storing data and/or software. The computing device 118 may also include one or more device drivers 166 for controlling one or more types of user interface devices and providing an interface between the user interface devices and components of the computing device 118 communicating with the user interface devices. Such user interface devices may include user input devices 168 (e.g., keyboard, keypad, touch screen, mouse, joystick, trackball, and the like) and user output devices 170 (e.g., display screen, printer, visual indicators or alerts, audible indicators or alerts, and the like). In various embodiments, the computing device 118 may be considered as including one or more user input devices 168 and user output devices 170, or at least communicating with them. The computing device 118 may also include one or more types of computer programs or software 172 contained in memory and/or on one or more types of computer-readable media 174. Computer programs or software may contain instructions (e.g., logic instructions) for performing all or part of any of the methods disclosed herein. Computer programs or software may include application software and system software. System software may include an operating system (e.g., a Microsoft Windows® operating system) for controlling and managing various functions of the computing device 118, including interaction between hardware and application software. In particular, the operating system may provide a graphical user interface (GUI) displayable via a user output device 170 such as a display screen, and with which a user may interact with the use of a user input device 168 such as a keyboard or a pointing device (e.g., mouse). The computing device 118 may also include one or more data acquisition/signal conditioning components 176 (as may be embodied in hardware, firmware and/or software) for receiving and processing ion measurement signals outputted by the ion detector 150, including formatting data for presentation in graphical form by the GUI.

It will be understood that FIGS. 1A and 1B are high-level schematic depictions of an example of an IM-MS system 100 and associated computing device 118 consistent with the present disclosure. Other components, such as additional structures, vacuum pumps, gas plumbing, ion optics, ion guides, electronics, and computer- or electronic processor-related components may be included as needed for practical implementations. It will also be understood that the computing device 118 is schematically represented in FIG. 1B as functional blocks intended to represent structures (e.g., circuitries, mechanisms, hardware, firmware, software, etc.) that may be provided. The various functional blocks and signal links have been arbitrarily located for purposes of illustration only and are not limiting in any manner. Persons skilled in the art will appreciate that, in practice, the functions of the computing device 118 may be implemented in a variety of ways and not necessarily in the exact manner illustrated in FIGS. 1A and 1B and described herein.

An IM-based system such as described above and illustrated in FIGS. 1A and 1B may be utilized to calculate the CCS of an ion of interest, based on calculating the drift time of the ion through the IMS drift cell. The drift time through the IMS drift cell may be calculated by measuring the total drift time of the ion (i.e., the duration of time from the point when the ion is pulsed into the drift cell to the point when the ion arrives at the ion detector), determining $t_0$ (the flight time of the ion from the exit of the drift cell to the ion detector), and subtracting $t_0$ from the total measured drift time. As noted above, conventionally this CCS analysis has required performing several IM experiments at several different drift voltages. According to the present disclosure, a method for measuring CCS may be performed within a single IM experiment, thus substantially improving the speed of the analysis. The method is particularly useful in cases where the speed of CCS measurement is highly desirable, such as when the analysis involves chromatography (e.g., LC) separation before IM analysis, where analytes are eluted as concentrated peaks that last only a few seconds.

In some embodiments, the method is based in part on the assumption that in a given IMS-based system, an ion after exiting the drift cell may experience some mobility-dominated (mobility-dependent) regions, mobility-independent regions, as well as some fixed delay, due to both physical and instrumental settings. A "mobility-dominated region" (or "mobility-dependent region") is a region outside the drift cell where ion flight time is influenced by CCS. A non-limiting example of a mobility dominated region is a region between the drift cell and the ion detector or mass analyzer in which gas pressure is relatively high, for example about $10^{-3}$ Torr or greater. Examples of such mobility dominated regions include, but are not limited to, relatively high-pressure ion funnels and collision cells that may be provided between the drift cell and the ion detector or mass analyzer. Hence, an ion processing device intermediately located between the drift cell and ion detector, such as described above in conjunction with FIG. 1A, may include one or more mobility-dominated regions. In this approximation, without limiting the scope of the present disclosure, the time for ions traveling in an electric field without gas pressure (or with negligible gas pressure), such as for example a quadrupole mass filter or ion guide, may be considered to be fixed or negligible. Another contribution to fixed time delay in practice could come from the delays associated with instrumental time measurements. Therefore, in some embodiments the time $t_0$, during which an ion spends outside the drift cell may be considered as including two components: a fixed delay time and an external (outside the drift cell) mobility-dependent drift time, which may be expressed as follows:

$$t_0 = t_{fix} + \beta_1 \gamma \Omega, \quad (6)$$

where $t_{fix}$ is the fixed delay time parameter which includes both mobility-independent flight time as well as instrument dependent time measurement delays, and $\beta_1 \gamma \Omega$ is the external mobility-dependent time. The value $\beta_1$ is a proportionality coefficient dependent on the gas pressures in the system, electrical fields, and geometry of the regions of the system outside the drift cell. The value $\gamma$ is a modified reduced mass coefficient, $\gamma = (m_I/(m_I + m_B))^{1/2}/q$, where $m_I$ is the mass of the ion, $m_B$ is the mass of the drift gas molecule, and q is the charge state of the ion. The value $\Omega$ is the CCS of the ion.

Consequently, the total measured (observed) drift time of an ion, $t_D$, is considered to include three components: the fixed delay time parameter, the external mobility-dependent drift time and an internal mobility-dependent time (i.e., the time actually taken by the ion to traverse the interior of the drift cell from entrance to exit). The total measured drift time $t_D$ may be expressed as follows:

$$t_D = t_{fix} + ((\beta_1 + \beta_2)\gamma \Omega), \quad (7)$$

where $\beta_2 \gamma \Omega$ is the drift time in the drift cell (internal mobility-dependent time), and $\beta_2$ is a proportionality coefficient dependent on the gas pressure, electrical field, and geometry of the drift cell itself.

From equation (7) it is seen that plotting total measured drift time $t_D$ values (y-axis) versus $\gamma \Omega$ values (x-axis) produces a straight line (i.e., y=mx+b) defined by two parameters, $t_{fix}$ and $\beta = (\beta_1 + \beta_2)$, where $\beta$ is the slope and $t_{fix}$ is the y-intercept as defined by eq. (7'):

$$t_D = t_{fix} + \beta \gamma \Omega, \quad (7')$$

The $\beta$-parameter is an instrument-dependent proportionality coefficient that is a combination of the first proportionality coefficient $\beta_1$ and the second proportionality coefficient $\beta_2$. $\beta$ may be referred to herein as a combined proportionality coefficient or a mobility-dependent drift time coefficient.

According to one embodiment of the method, the two parameters $t_{fix}$ and $\beta$ may be determined by acquiring reference data points ($\gamma \Omega$, $t_D$) from a group of reference ions having known CCSs (reference CCSs), and performing a simple linear regression technique on the plot (equation (7)) of the reference data points. The known CCSs are obtained prior to analysis of a sample ion of unknown CCS. The known CCSs may be obtained from performing a conventional technique based on iterative measurement of drift times such as described above in the Background section of the present disclosure, using the same buffer gas as is subsequently used in the analysis of the sample ion of unknown CCS. The total measured drift times $t_D$ are then acquired by running the reference molecules through the same IM-MS system (with the same ensemble of physical structures and devices) to be utilized for analyzing a sample ion of unknown CCS, and under substantially the same operating conditions (e.g., buffer gas composition, pressure, temperature, drift field strength, etc.) utilized for measuring the total drift time of the sample ion.

The unknown CCS of a sample ion may be calculated in conjunction with determining the parameters $t_{fix}$ and $\beta$ for the IM-MS system. This may be done by performing a single IM experiment on the sample ion and measuring its total drift time $t_D$. That is, the sample ion need only be processed once, through the same IM-MS system and under the same operating parameters utilized in measuring the total drift times $t_D$ of the reference ions. Once the total measured drift time $t_D$ of the sample ion has been acquired, its CCS may be calculated from the following equation, which is a rearrangement of equation (7):

$$\Omega = (t_D - t_{fix})/\beta \gamma. \quad (8)$$

As noted above, the unknown CCS of the sample ion may be calculated "in conjunction with" determining the parameters $t_{fix}$ and $\beta$. Hence, the total drift time $t_D$ of the sample ion may be measured "in conjunction with" measuring the total drift times $t_D$ of the reference ions—that is, before, during, or after measuring the total drift times $t_D$ of the reference ions. Thus, in some embodiments, the reference ions may be co-introduced with the sample ion into the drift cell. In this case, the total measured drift times $t_D$ of both the reference ions and the sample ion are acquired in the same frame. In each frame acquired, the parameters $t_{fix}$ and $\beta$ may be identified by applying a simple linear regression technique to the plot of reference data points ($\gamma \Omega$, $t_D$) corresponding to the reference ions. For the sample ion with unknown CCS in the same frame, the CCS may be identified from the total measured drift times $t_D$ of the sample ion according to equation (8). In some embodiments, the reference ions co-introduced with the sample ion may be so-called mass-reference ions (e.g., internal calibrants) that are typically co-introduced with sample ions for the purpose of mass calibration of the MS instrumentation.

In other embodiments, the reference ions may be introduced into the drift cell before or after the sample ion with unknown CCS. As long as instrument pressures and voltages are sufficiently constant for the duration of the complete experiment, the methods as described herein may be utilized for calculating the unknown CCS.

The use of two reference compounds may be sufficient to establish values for the parameters $t_{fix}$ and $\beta$. Using more than two reference compounds may improve the accuracy of the method. Moreover, using more than two reference compounds enables the calculation of the regression coefficient $R^2$ of the simple linear regression performed. A regression coefficient calculated to be close to unity (1) indicates high correlation among the data points within the reference ion mobility range.

In some embodiments, the $t_{fix}$ parameter may be negligibly small, in which case it may be practical to set $t_{fix}$ to zero and utilize simple linear regression without the intercept term to identify the β parameter.

In some embodiments, the drift gas may be a mixture of gases. In this case, in the equation for $\gamma=(m_I/(m_I+m_B))^{1/2}/q$ the buffer gas mass value $m_B$ may be treated as an unknown parameter, which may be identified, for example, by maximizing the regression coefficient R from the linear regression plots of $t_D$ vs. γΩ with three or more referenced ions present. It is recognized that according to this embodiment even a single drift gas can be treated as a mixture of gases since background gases are always present in the drift tube and in practice 100% drift gas purity within the drift tube can be difficult to achieve.

Although certain embodiments of methods disclosed herein are based on some theoretical considerations that there are well defined regions in the system where ions experience mobility-dependent regions as well as mobility-independent regions, the broader aspects of the methods are not limited to these assumptions.

Example 1

This Example entailed the operation of an IM-MS system structured in accordance with the embodiment generally described above and illustrated in FIG. 1A. Ten reference compounds with known (reference) CCSs in nitrogen ($N_2$) buffer gas were infused and transmitted through the system, and their drift times were measured according to the method described above. TABLE 1 below provides the data corresponding to these reference compounds.

TABLE 1

| CCS ref. compound | m/z | CCS (Å²), referenced | drift time $t_D$ (ms) |
| --- | --- | --- | --- |
| 1 | 118 | 121.5 | 14.86 |
| 2 | 322 | 153.2 | 20.2 |
| 3 | 622 | 202.9 | 27.24 |
| 4 | 922 | 243.0 | 33.01 |
| 5 | 1222 | 281.7 | 38.39 |
| 6 | 1522 | 315.7 | 43.22 |
| 7 | 1822 | 348.6 | 47.78 |
| 8 | 2122 | 379.8 | 52.16 |
| 9 | 2422 | 408.3 | 56.36 |
| 10 | 2722 | 435.7 | 60.32 |

Figure 2:
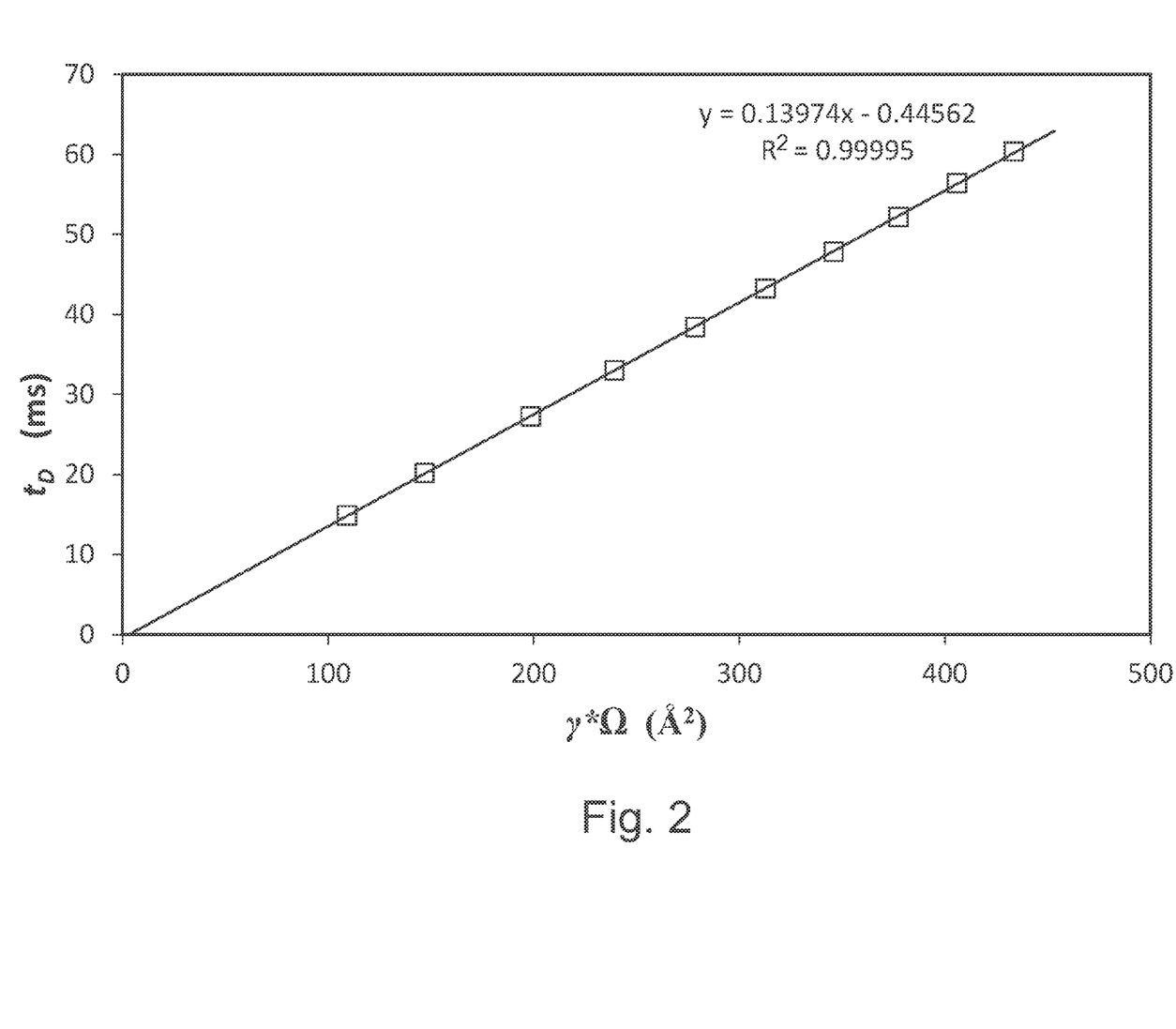
FIG. 2 is a plot of $t_D$ vs. $\gamma\Omega$ for reference compounds utilized in conjunction with measuring the collision cross section of an ion according to a method disclosed herein.

FIG. 2 is a plot of $t_D$ vs. γΩ for these reference compounds. Simple linear regression was applied to the data according to the method described above, yielding a straight line defined by y=0.1397x−0.4456. Thus, the parameters β and $t_{fix}$ were found to be 0.1397 and −0.4456, respectively. The regression coefficient $R^2$ was found to be 0.9999, suggesting a very high linear correlation existing between the data described by the coordinates in the mobility range.

To evaluate the method, two additional compounds with known CCSs were infused immediately after the ten reference compounds and their drift times were measured. Using the values found for β and $t_{fix}$, the CCSs of these two compounds were calculated according to the method described above. TABLE 2 below provides the data corresponding to these two compounds.

TABLE 2

| Compound | m/z | drift time (ms) | CCS (Å²), literature referenced | CCS (Å²), calculated | Error, % |
| --- | --- | --- | --- | --- | --- |
| Colchicine | 400.44 | 25.99 | 196.2 | 196.9 | 0.27 |
| Ondansetrone | 294.40 | 22.62 | 173.2 | 173.4 | 0.26 |

Thus, the experimental error is below 0.5% for both ions, demonstrating the accuracy of the method disclosed herein.

Example 2

This Example again entailed the operation of an IM-MS system structured in accordance with the embodiment generally described above and illustrated in FIG. 1A. In this Example, six reference compounds with known CCSs in nitrogen ($N_2$) buffer gas (the same first six compounds utilized in Example 1) were infused and transmitted through the system, and their drift times were measured as a CCS calibration standard according to the method described above. TABLE 3 below provides the data corresponding to these reference compounds.

TABLE 3

| CCS ref. compound | m/z | CCS (Å²), referenced | drift time $t_D$ (ms) |
| --- | --- | --- | --- |
| 1 | 118 | 121.5 | 12.17 |
| 2 | 322 | 153.2 | 16.46 |
| 3 | 622 | 202.9 | 22.14 |
| 4 | 922 | 243.0 | 26.82 |
| 5 | 1222 | 281.7 | 31.2 |
| 6 | 1522 | 315.7 | 35.17 |

Figure 3:
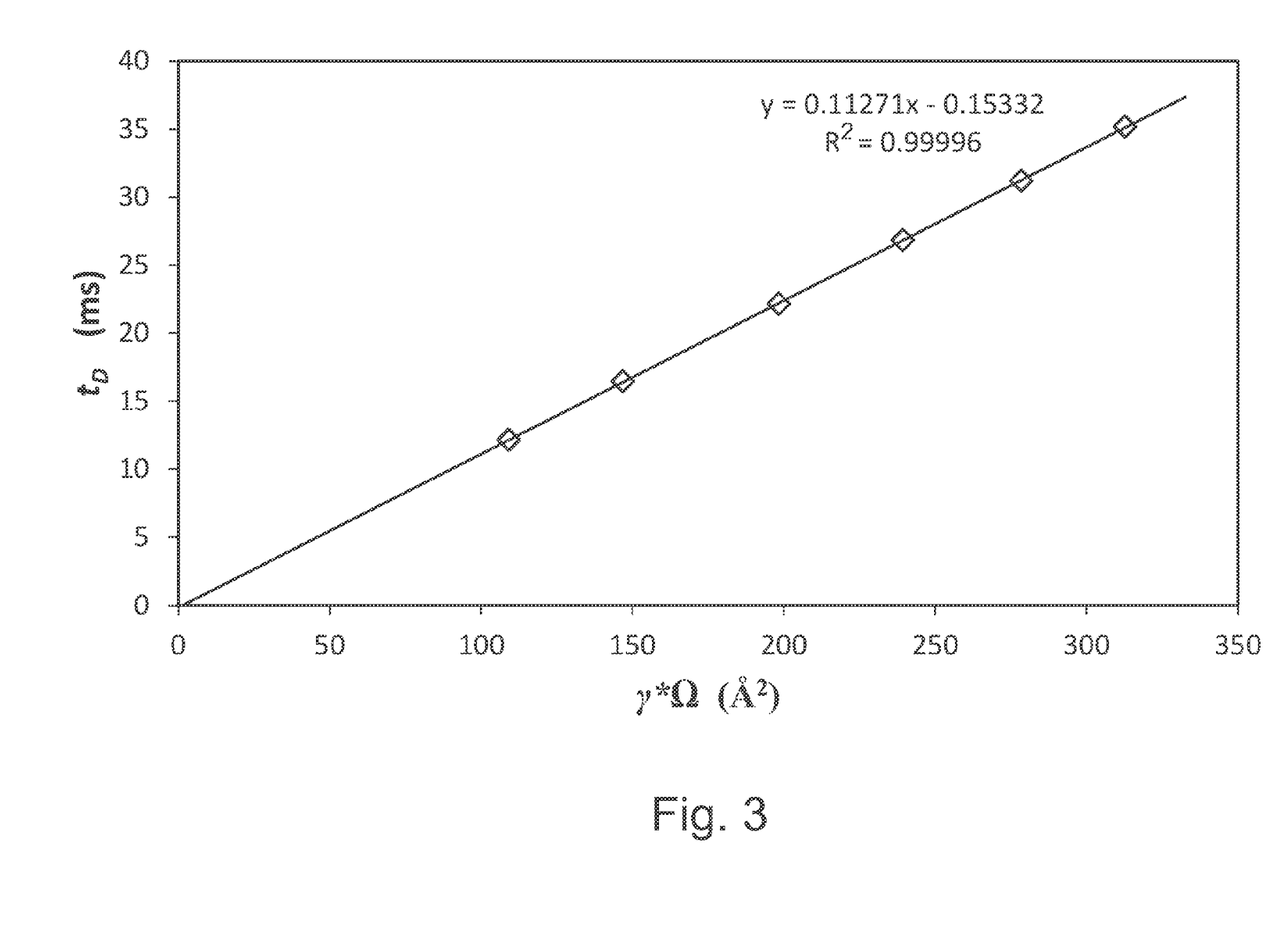
FIG. 3 is another plot of $t_D$ vs. $\gamma\Omega$ for reference compounds utilized in conjunction with measuring the collision cross section of an ion according to a method disclosed herein.

FIG. 3 is a plot of $t_D$ vs. γΩ for these reference compounds. Simple linear regression was applied to the data according to the method described above, yielding a straight line defined by y=0.11271x−0.15332. Thus, the parameters β and $t_{fix}$ were found to be 0.11271 and −0.15332, respectively. The regression coefficient $R^2$ was found to be 0.99996, again suggesting a very high linear correlation existing between the data described by the coordinates in the mobility range.

To evaluate the method, several peptides with known CCSs were infused immediately after the six reference compounds and their drift times were measured. Using the values found for ft and $t_{fix}$, the CCSs of these two compounds were calculated according to the method described above. TABLE 4 below provides the data corresponding to these peptides.

TABLE 4

| Compound | q | mass | drift time (ms) | CCS (Å²), referenced | CCS (Å²), measured | Error, % |
| --- | --- | --- | --- | --- | --- | --- |
| peptide 1 | 1 | 1371 | 40.89 | 364.1 | 366.6 | 0.70 |
| peptide 1 | 2 | 1371 | 21.74 | 387.3 | 390.0 | 0.68 |
| peptide 2 | 1 | 927 | 33.65 | 301.0 | 301.7 | 0.23 |
| peptide 2 | 2 | 927 | 18.6 | 332.9 | 333.7 | 0.23 |
| peptide 3 | 1 | 1149 | 37.26 | 332.4 | 334.1 | 0.51 |
| peptide 3 | 2 | 1149 | 19.93 | 355.6 | 357.5 | 0.53 |
| peptide 4 | 2 | 820 | 24.37 | 433.4 | 437.1 | 0.85 |

Thus, the experimental error is below 1% for all ions, again demonstrating the accuracy of the method disclosed herein.

In some embodiments of the method, measured CCSs of one or more ions may be further corrected (calibrated) based on a single ion with a known CCS that was present in the same frame as the ions whose CCSs are to be further corrected. That is, the in-frame ion with the known CCS may be utilized as a reference ion for correcting the measured CCSs of the other ions. The correction may be performed according to equation (8) by linear scaling for the β-parameter to the scale that results in the measured CCS of the in-frame reference ion exactly matching the known CCS of the in-frame reference ion. For example, if the singly-charged peptide 1 of TABLE 4 above is utilized as the in-frame reference ion, then all measured CCS values of the other ions measured in the same frame are scaled up by 0.70%. TABLE 5 below presents the reduced experimental errors after performing this fine correction.

TABLE 5

| Compound | q | Corrected CCS (Å$^2$) | Error, % |
|---|---|---|---|
| peptide 1 | 1 | 364.1 | 0.00 |
| peptide 1 | 2 | 387.3 | 0.00 |
| peptide 2 | 1 | 299.7 | −0.4 |
| peptide 2 | 2 | 331.4 | −0.4 |
| peptide 3 | 1 | 331.8 | −0.2 |
| peptide 3 | 2 | 355.1 | −0.2 |
| peptide 4 | 2 | 434.1 | 0.2 |

Thus, after the fine correction the all measured CCSs are within 0.5% of the referenced CCSs.

In another embodiment, equation (7) may be generalized to include second-order terms. Second-order terms may take into consideration external mass-dependent flight time, i.e., the time an ion takes to travel through a mobility-independent region, between the drift cell exit and the ion detector. A mobility-independent region is a region outside the drift cell where ion flight time is primarily influenced by its m/z ratio and electric field strength. A non-limiting example of a mobility-independent region is a region between the drift cell and the ion detector or mass analyzer in which gas pressure is relatively low (i.e., high vacuum), for example about $10^{-3}$ Torr or lower and contains an electric field. Examples of such mobility-independent regions include, but are not limited to, high vacuum electrostatic regions (such as ion optics regions), high vacuum ion guides, and mass filters (e.g., quadrupole mass filters) that may be provided between the drift cell and the ion detector. In the present context, the term "high vacuum" ion guide encompasses a collision cell operating at high vacuum, for example operating to transmit ions without inducing collision-induced dissociation, without substantial ion cooling and/or focusing. Hence, an ion processing device intermediately located between the drift cell and ion detector, such as described above in conjunction with FIG. 1A, may include one or more mobility-independent regions as well as mobility-dominated regions. In this embodiment, the total measured drift time may be expressed as follows:

$$t_{D'} = t_{fix} + (\beta_1 + \beta_2)\gamma\Omega + A(m_I/q)^{1/2}, \qquad (9)$$

where $A(m_I/q)^{1/2}$ is the mobility-independent or mass-dependent flight time, A is a (third) proportionality coefficient (mobility-independent flight time coefficient) dependent on the electric field (E), $m_I$ is the mass of the ion, and q is the charge state of the ion. It will be noted that in equation (9), the fixed delay term $t_{fix}$ accounts for instrument dependent time measurement delays as in the case of (7), but in equation (9) the flight time term $A(m_I/q)^{1/2}$ accounts for the mobility-independent flight time. That is, by employing equation (9) the mobility-independent flight time is not assumed to be constant or negligible, although typically the value for mobility-independent flight time is comparatively small. For example, in a case where the final mass analyzer in the system is a TOF analyzer, equation (9) does not take into consideration the flight time through the TOF analyzer. Instead, $t_{D'}$ spans the flight time from the entrance of the drift cell to the pusher region of the TOF analyzer. The values for the fixed delay time parameter $t_{fix}$ and the proportionality coefficients β (again, $\beta = \beta_1 + \beta_2$) and A may be identified from a set of at least three reference ions with known mass $m_I$, CCS Ω, and charge state q, by solving the above equation (9) by the least squares method using the known parameters (mass $m_I$, CCS Ω, and charge state q) of the three or more reference ions. Utilizing more than three reference ions may improve the accuracy of the least squares technique. Then, the CCS of an ion of interest may be calculated from a generalized form of equation (8):

$$\Omega = (t_D - t_{fix} - (A(m_I/q)^{1/2}))/\beta\gamma. \qquad (10)$$

From the foregoing description, it is seen that methods disclosed herein for measuring the CCS of a sample ion may be performed within a single IM experiment, an thus may offer a significant improvement in the speed of analysis over conventional methods. Calculation of CCSs according to the methods disclosed herein may be useful for compound identification. CCS values acquired in this manner may thus serve as orthogonal data in conjunction with other analyte-specific data such as IM drift times, m/z ratios, etc. The choice between utilizing equation (8) or the more generalized equation (10) and their associated methods described above to calculate CCS may depend on a variety of factors, such as the degree of accuracy desired or required, the combination of components and regions existing in the particular system being employed for sample analysis, etc.

Exemplary Embodiments

Exemplary embodiments provided in accordance with the presently disclosed subject matter include, but are not limited to, the following:

1. A method for measuring the collision cross section (CCS) of a sample ion, the method comprising: measuring a total drift time taken by the sample ion to travel from an entrance of an ion mobility spectrometry drift cell to an ion detector outside an exit of the drift cell; and calculating the CCS of the sample ion from the following equation: $\Omega = (t_D - t_{fix})/\beta\gamma$, wherein Ω is the CCS, $t_D$ is the total drift time measured, $t_{fix}$ is a fixed delay time parameter, β is a proportionality coefficient, and $\gamma = (m_I/(m_I + m_B))^{1/2}$, wherein $m_I$ is the mass of the sample ion, $m_B$ is the mass of a drift gas molecule in the drift cell, and q is the charge state of the sample ion.

2. The method of embodiment 1, wherein the mobility-dependent region comprises a region at a gas pressure of about $10^{-3}$ Torr or greater.

3. The method of embodiment 2, wherein the mobility-dependent region comprises an ion funnel or a collision cell.

4. The method of any of the preceding embodiments, wherein the fixed delay time β accounts for instrument dependent time measurement delay, or for mobility-independent flight time, or for both time measurement delay and mobility-independent flight time.

5. The method of any of the preceding embodiments, comprising determining the proportionality coefficient β.

6. The method of embodiment 5, wherein determining the proportionality coefficient β comprises measuring respective total drift times taken by a plurality of reference ions of respective known CCSs to travel through the drift cell to the ion detector, under substantially the same operating conditions utilized for measuring the total drift time of the sample ion.

7. The method of embodiment 6, wherein determining the proportionality coefficient β comprises applying simple linear regression of a plurality of data points, each data point being a total drift time measured for a respective reference ion as a function of γΩ, and wherein: Ω is the known CCS of the reference ion; $\gamma=(m_I/(m_I+m_B))^{1/2}/q$, wherein $m_I$ is the mass of the reference ion, $m_B$ is the mass of a drift gas molecule in the drift cell, and q is the charge state of the reference ion; and the proportionality coefficient is a slope of a line passing through the data points.

8. The method of embodiment 7, wherein the drift cell contains a mixture of drift gases, and applying simple linear regression comprises calculating a value for $m_B$.

9. The method of embodiment 7 or 8, comprising determining the fixed delay time $t_{fix}$ as a y-intercept of the line.

10. The method of any of the preceding embodiments, wherein measuring the total drift times of the reference ions is done before, during, or after measuring the total drift time of the sample ion.

11. The method of any of the embodiments 6 to 10, wherein the ion detector is part of or communicates with a mass spectrometer, and the reference ions are mass-reference ions suitable for calibrating the mass spectrometer.

12. The method of any of the preceding embodiments, comprising injecting a plurality of sample ions into the drift cell at the same time, measuring the total drift times of the respective sample ions, calculating the CCSs of respective sample ions, determining a percent error between the calculated CCS of at least one selected sample ion and a reference CCS value for the selected sample ion, and scaling the calculated CCSs of the respective sample ions by the percent error.

13. The method of any of the preceding embodiments, wherein calculating the CCS is further based on a mobility-independent flight time taken by the sample ion to travel through a mobility-independent region between the drift cell and the ion detector.

14. The method of embodiment 13, wherein the mobility-independent region comprises a region at a gas pressure of about $10^{-3}$ Torr or lower.

15. The method of embodiment 14, wherein the mobility-independent region comprises at least one of: an ion optics region; an ion guide; a mass filter; and a quadrupole mass analyzer.

16. The method of any of the preceding embodiments, wherein calculating the CCS comprises accounting for the mobility-independent flight time according to the following equation: $\Omega=(t_D-t_{fix}-(A(m_I/q)^{1/2}))/\beta\gamma$, wherein $A(m_I/q)^{1/2}$ is the mobility-independent flight time, and A is a proportionality coefficient dependent on electric field strength in the mobility-independent region.

17. The method of embodiment 16, comprising determining the fixed delay time $t_{fix}$ and the proportionality coefficients A and β by measuring respective total drift times taken by a three or more reference ions of respective known CCSs to travel through the drift cell to the ion detector, under substantially the same operating conditions utilized for measuring the total drift time of the sample ion, and solving the equation of embodiment 16 by a least squares method using the known parameters mass $m_I$, CCS Ω, and charge state q of the respective three or more reference ions.

18. A method for acquiring spectral data from a sample, the method comprising: producing a plurality of sample ions from the sample; transmitting the sample ions through the drift cell to separate sample ions of differing CCSs; transmitting the sample ions from the drift cell through a mass analyzer to separate sample ions of differing m/z ratios; transmitting the sample ions from the mass analyzer to the ion detector; calculating CCSs of the respective sample ions according to the method of any of the preceding embodiments; and generating a drift time spectrum and a mass spectrum from signals outputted by the ion detector.

19. An ion mobility-mass spectrometry (IM-MS) system configured for performing all or part of the method of any of the preceding embodiments.

20. An ion mobility-mass spectrometry (IM-MS) system, comprising: an IM drift cell comprising a drift cell entrance and a drift cell exit; an intermediate region following the drift cell exit and comprising a mobility-dependent region; an MS detector following the intermediate region; and a computing device configured for measuring the collision cross section (CCS) of a sample ion by: measuring a total drift time taken by the sample ion to travel from the drift cell entrance to the MS detector; and calculating the CCS of the sample ion based on the total drift time measured and on a proportionality coefficient relating to a drift time taken by the sample ion to travel through the drift cell and through the mobility-dependent region.

21. The IM-MS system of embodiment 20, wherein the mobility-dependent region comprises a region at a gas pressure of about $10^{-3}$ Torr or greater.

22. A system for measuring the collision cross section (CCS) of a sample ion, the system comprising: at least a processor and a memory configured for performing all or part of the method of any of the preceding embodiments.

23. The system of embodiment 22, comprising a user output device, a user input device, or both a user output device and a user input device.

24. The system of embodiment 22 or 23, comprising an ion detector configured for transmitting ion measurement signals to the processor.

25. The system of embodiment 24, comprising an ion mobility spectrometer and a mass spectrometer communicating with the ion detector.

26. A computer-readable storage medium comprising instructions for performing all or part of the method of any of the preceding embodiments.

27. A system comprising the computer-readable storage medium of embodiment 26.

Methods for measuring the CCS of an ion such as described above and illustrated in the Figures may be performed (carried out), for example, in a system that includes a processor and a memory as may be embodied in, for example, a computing device communicating with a user input device and a user output device. In some embodiments, the system for measuring the CCS of an ion (or an associated computing device) may be considered as including the user input device and/or the user output device. An IM-MS system such as described above and illustrated in FIG. 1A may include, or be part of, or communicate with a system for measuring the CCS of an ion. As used herein, the term "perform" or "carry out" may encompass actions such as controlling and/or signal or data transmission. For example, the computing device 118 or a processor thereof may perform a method step by controlling another component involved in performing the method step. Performing or controlling may involve making calculations, or sending and/or receiving signals (e.g., control signals, instructions, measurement signals, parameter values, data, etc.).

As used herein, an "interface" or "user interface" is generally a system by which users interact with a computing device. An interface may include an input (e.g., a user input device) for allowing users to manipulate a computing device, and may include an output (e.g., a user output device) for allowing the system to present information and/or data, indicate the effects of the user's manipulation, etc. An example of an interface on a computing device includes a graphical user interface (GUI) that allows users to interact with programs in more ways than typing. A GUI typically may offer display objects, and visual indicators, as opposed to (or in addition to) text-based interfaces, typed command labels or text navigation to represent information and actions available to a user. For example, an interface may be a display window or display object, which is selectable by a user of a computing device for interaction. The display object may be displayed on a display screen of a computing device and may be selected by and interacted with by a user using the interface. In one non-limiting example, the display of the computing device may be a touch screen, which may display the display icon. The user may depress the area of the touch screen at which the display icon is displayed for selecting the display icon. In another example, the user may use any other suitable interface of a computing device, such as a keypad, to select the display icon or display object. For example, the user may use a track ball or arrow keys for moving a cursor to highlight and select the display object.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the computing device 118 schematically depicted in FIGS. 1A and 1B. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the computing device 118 in FIGS. 1A and 1B), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program may be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for measuring the collision cross section (CCS) of a sample ion, the method comprising:
    measuring a total drift time taken by the sample ion to travel from an entrance of an ion mobility spectrometry drift cell to an ion detector outside an exit of the drift cell; and
    calculating the CCS of the sample ion from the following equation:

$$\Omega = (t_D - t_{fix})/\beta\gamma,$$

wherein $\Omega$ is the CCS, $t_D$ is the total drift time measured, $t_{fix}$ is a fixed delay time parameter, $\beta$ is a proportionality coefficient relating to a drift time taken by the sample ion to travel through the drift cell and through a mobility-dependent region outside the drift cell, and $\gamma=(m_I/(m_I+m_B))^{1/2}/q$, wherein $m_I$ is the mass of the sample ion, $m_B$ is the mass of a drift gas molecule in the drift cell, and q is the charge state of the sample ion.

2. The method of claim 1, wherein the mobility-dependent region comprises a region selected from the group consisting of: a region at a gas pressure of about $10^{-3}$ Torr or greater; an ion funnel; a collision cell; and a combination of two or more of the foregoing.

3. The method of claim 1, wherein the fixed delay time $t_{fix}$ accounts for instrument dependent time measurement delay, or for mobility-independent flight time, or for both time measurement delay and mobility-independent flight time.

4. The method of claim 1, comprising determining the proportionality coefficient $\beta$.

5. The method of claim 4, wherein determining the proportionality coefficient $\beta$ comprises measuring respective total drift times taken by a plurality of reference ions of respective known CCSs to travel through the drift cell to the ion detector, under substantially the same operating conditions utilized for measuring the total drift time of the sample ion.

6. The method of claim 5, wherein determining the proportionality coefficient $\beta$ comprises applying simple linear regression of a plurality of data points, each data point being a total drift time measured for a respective reference ion as a function of $\gamma\Omega$, and wherein:
$\Omega$ is the known CCS of the reference ion;
$\gamma=(m_I/(m_I+m_B))^{1/2}/q$, wherein $m_I$ is the mass of the reference ion, $m_B$ is the mass of a drift gas molecule in the drift cell, and q is the charge state of the reference ion; and
the proportionality coefficient is a slope of a line passing through the data points.

7. The method of claim 6, wherein the drift cell contains a mixture of drift gases, and applying simple linear regression comprises calculating a value for $m_B$.

8. The method of claim 6, comprising determining the fixed delay time $t_{fix}$ as a y-intercept of the line.

9. The method of claim 5, wherein measuring the total drift times of the reference ions is done before, during, or after measuring the total drift time of the sample ion.

10. The method of claim 5, wherein the ion detector is part of or communicates with a mass spectrometer, and the reference ions are mass-reference ions suitable for calibrating the mass spectrometer.

11. The method of claim 1, comprising injecting a plurality of sample ions into the drift cell at the same time, measuring the total drift times of the respective sample ions, calculating the CCSs of respective sample ions, determining a percent error between the calculated CCS of at least one selected sample ion and a reference CCS value for the selected sample ion, and scaling the calculated CCSs of the respective sample ions by the percent error.

12. The method of claim 1, wherein calculating the CCS is further based on a mobility-independent flight time taken by the sample ion to travel through a mobility-independent region between the drift cell and the ion detector.

13. The method of claim 12, wherein the mobility-independent region comprises a region selected from the group consisting of: a region at a gas pressure of about $10^{-3}$ Torr or lower; an ion optics region; an ion guide; a mass filter; and a quadrupole mass analyzer; and a combination of two or more of the foregoing.

14. The method of claim 1, wherein calculating the CCS comprises accounting for the mobility-independent flight time according to the following equation:

$$\Omega=(t_D-t_{fix}-(A(m_I/q)^{1/2}))/\beta\gamma,$$

wherein $A(m_I/q)^{1/2}$ is the mobility-independent flight time, and A is a proportionality coefficient dependent on electric field strength in the mobility-independent region.

15. The method of claim 14, comprising determining the fixed delay time $t_{fix}$ and the proportionality coefficients A and $\beta$ by measuring respective total drift times taken by three or more reference ions of respective known CCSs to travel through the drift cell to the ion detector, under substantially the same operating conditions utilized for measuring the total drift time of the sample ion, and solving the equation of claim 14 by a least squares method using the known parameters mass $m_I$, CCS $\Omega$, and charge state q of the respective three or more reference ions.

16. A method for acquiring spectral data from a sample, the method comprising:
producing a plurality of sample ions from the sample;
transmitting the sample ions through the drift cell to separate sample ions of differing CCSs;
transmitting the sample ions from the drift cell through a mass analyzer to separate sample ions of differing m/z ratios;
transmitting the sample ions from the mass analyzer to the ion detector;
calculating CCSs of the respective sample ions according to the method of claim 1; and
generating a drift time spectrum and a mass spectrum from signals outputted by the ion detector.

17. An ion mobility-mass spectrometry (IM-MS) system configured for performing the method of claim 1.

18. An ion mobility-mass spectrometry (IM-MS) system, comprising:
an IM drift cell comprising a drift cell entrance and a drift cell exit;
an intermediate region following the drift cell exit and comprising a mobility-dependent region;
an ion detector following the intermediate region; and
a computing device configured for measuring the collision cross section (CCS) of a sample ion by:
measuring a total drift time taken by the sample ion to travel from the drift cell entrance to the ion detector; and
calculating the CCS of the sample ion from the following equation:

$$\Omega=(t_D-t_{fix})/\beta\gamma,$$

wherein $\Omega$ is the CCS, $t_D$ is the total drift time measured, $t_{fix}$ is a fixed delay time parameter, $\beta$ is a proportionality coefficient relating to a drift time taken by the sample ion to travel through the drift cell and through a mobility-dependent region outside the drift cell, and $\gamma=(m_I/m_I+m_B))^{1/2}/q$, wherein $m_I$ is the mass of the sample ion, $m_B$ is the mass of a drift gas molecule in the drift cell, and q is the charge state of the sample ion.

19. The IM-MS system of claim 18, wherein the fixed delay time $t_{fix}$ accounts for instrument dependent time measurement delay, or for mobility-independent flight time, or for both time measurement delay and mobility-independent flight time.

20. The IM-MS system of claim 18, wherein the computing device is configured for calculating the CCS of the sample ion further based on a mobility-independent flight time taken by the sample ion to travel through a mobility-independent region between the drift cell and the ion detector.

* * * * *